United States Patent
Möri et al.

(10) Patent No.: US 7,239,941 B2
(45) Date of Patent: Jul. 3, 2007

(54) DEVICE FOR PROGRAMMING A PUMP USED TO INJECT MEDICAMENTS

(75) Inventors: Peter Möri, Walperswil (CH); Heinz Wüthrich, Worblaufen (CH); Beat Stulz, Fribourg (CH); Claude Clement, Lussy-sur-Morges (CH)

(73) Assignee: Precimedix SA, Neuchatel (CH)

( * ) Notice: Subject to any disclaimer, the term of this patent is extended or adjusted under 35 U.S.C. 154(b) by 0 days.

(21) Appl. No.: 10/524,872

(22) PCT Filed: Jul. 25, 2003

(86) PCT No.: PCT/CH03/00505

§ 371 (c)(1),
(2), (4) Date: Feb. 14, 2005

(87) PCT Pub. No.: WO2004/016304

PCT Pub. Date: Feb. 26, 2004

(65) Prior Publication Data

US 2005/0261805 A1    Nov. 24, 2005

(30) Foreign Application Priority Data

Aug. 14, 2002    (EP)   .................................. 02405693

(51) Int. Cl.
G05D 7/00    (2006.01)
A61M 1/00    (2006.01)

(52) U.S. Cl. ........................................ 700/283; 604/30

(58) Field of Classification Search .................. 604/19, 604/30, 31, 65–67, 890.1–892.1; 700/282–285
See application file for complete search history.

(56) References Cited

U.S. PATENT DOCUMENTS

| 4,624,661 A | * | 11/1986 | Arimond | ..................... 604/151 |
| 4,722,734 A | * | 2/1988 | Kolln | ......................... 604/151 |
| 5,246,422 A |   | 9/1993 | Favre | .......................... 604/110 |
| 5,338,157 A |   | 8/1994 | Blomquist | ..................... 417/2 |

(Continued)

FOREIGN PATENT DOCUMENTS

EP    1 249 606    10/2002

(Continued)

*Primary Examiner*—Maria N. Von Buhr
(74) *Attorney, Agent, or Firm*—Townsend M. Belser, Jr.; Nexsen Pruet Adams Kleemeier, LLC

(57) ABSTRACT

The invention relates to a device for programming a pump used to inject medicaments. Said pump comprises two connectable units, namely: (i) a cartridge unit (12) which contains the liquid to be injected and which comprises an electronic memory unit (36) that is intended to contain data relating to the treatment that the patient is to receive and (ii) a pump unit (10) comprising actuation means (18) which act on the aforementioned cartridge unit (12) in order to convey the liquid outwards and a microprocessor which is used to control said actuation means using the data contained in the memory unit (36). The inventive device comprises (a) a computer (46) which is used to produce the above-mentioned data and (b) a first interface (50) which can be connected to the computer in order to receive said data and designed to be connected to the cartridge unit (12) in place of the pump unit (10) in order to introduce the data into the memory unit (36).

8 Claims, 3 Drawing Sheets

U.S. PATENT DOCUMENTS

| | | | |
|---|---|---|---|
| 5,485,408 A | 1/1996 | Blomquist | 703/9 |
| 5,582,593 A * | 12/1996 | Hultman | 604/65 |
| 5,658,250 A | 8/1997 | Blomquist et al. | 604/65 |
| 5,669,877 A | 9/1997 | Blomquist | 604/67 |
| 5,739,508 A | 4/1998 | Uber, III | 235/375 |
| 5,788,669 A | 8/1998 | Peterson | 604/65 |
| 5,810,771 A | 9/1998 | Blomquist | 604/65 |
| 5,876,370 A | 3/1999 | Blomquist | 604/65 |
| 5,920,054 A | 7/1999 | Uber, III | 235/375 |
| 5,935,099 A | 8/1999 | Peterson et al. | 604/65 |
| 6,024,539 A | 2/2000 | Blomquist | 417/63 |
| 6,039,251 A * | 3/2000 | Holowko et al. | 235/380 |
| 6,109,895 A | 8/2000 | Ray et al. | 417/477.2 |
| 6,241,707 B1 | 6/2001 | Dysarz | 604/110 |
| 6,641,562 B1 * | 11/2003 | Peterson | 604/141 |
| 6,668,196 B1 * | 12/2003 | Villegas et al. | 607/60 |
| 6,694,191 B2 * | 2/2004 | Starkweather et al. | 607/60 |
| 6,733,446 B2 * | 5/2004 | Lebel et al. | 600/300 |
| 2001/0031944 A1 | 10/2001 | Peterson et al. | 604/65 |
| 2002/0183693 A1 | 12/2002 | Peterson et al. | 604/151 |
| 2003/0050535 A1 * | 3/2003 | Bowman et al. | 600/300 |
| 2003/0052196 A1 * | 3/2003 | Fuchs | 239/338 |
| 2003/0083645 A1 * | 5/2003 | Angel et al. | 604/890.1 |

FOREIGN PATENT DOCUMENTS

| | | |
|---|---|---|
| EP | 02 405639.2 | 1/2004 |
| FR | 2753235 | 3/1998 |

* cited by examiner

DEVICE FOR PROGRAMMING A PUMP USED TO INJECT MEDICAMENTS

The present invention concerns the field of miniaturized pumps for injecting medicaments into a patient's body according to a prescribed program. It relates, more particularly, to a device for programming a medical pump made up of a pump unit and of a cartridge unit containing the medicament, which units are connected to one another in a detachable manner.

Miniaturized pumps for medical use have been known for some years. Being light and small, they are carried by the patient in a discreet and comfortable manner and allow the patient to administer, subcutaneously or intravenously, and either continuously or according to a specified program, controlled quantities of medicinal solutions, without said patient having to be confined to bed and connected up to a bulky, expensive and noisy apparatus.

Such pumps are often of the rotary peristaltic type. The principle of these pumps consists in employing a deformable plastic tube linked to a reservoir containing the medicinal solution and in squeezing it locally against a bearing piece of rounded shape by means of press rollers mounted on a rotor driven by a motor acting via a gear train. The liquid is thus sucked from the reservoir and pushed toward the outlet so as to be injected into the patient's body.

Document FR 2 753 235, for example, describes cartridge pumps of this type.

In designing these pumps, it is particularly important to be mindful of their ease of programming. As they are intended to be used in particular in a non-hospital environment, it must in fact be possible for them to be operated safely by any care provider, or even by the patient himself or herself, without their having received special training or having to read lengthy and complicated directions for use. However, these requirements of user-friendliness and safety are rarely satisfied by the pumps presently available on the market. The risk, therefore, is that they remain an item of hospital equipment reserved for a small number of nurses, thus robbing them of a large part of the benefit they offer.

Document EP-02 405639.2 describes a programmable cartridge pump immediately usable by any person, without the need for any training or for any particular knowledge. It is made up of two connectable units, namely:
- a cartridge unit which contains a liquid to be injected and which comprises an electronic memory intended to contain data relating to the treatment that the patient is to receive, and
- a pump unit comprising actuation means which act on the cartridge unit in order to convey the liquid outward, a microprocessor which is used to control said means using the data contained in said memory, and a source of electrical energy.

To ensure that a pump of the above-described type responds optimally to the requirements in respect of ease of use and safety, it has to be programmed by means of a device satisfying the same requirements.

The object of the present invention is therefore to provide such a programming device comprising:
- a computer which is used to produce the data relating to the treatment that the patient is to receive, and
- an interface which can be connected to the computer in order to receive said data and which is designed to be connected to the cartridge unit in place of the pump unit in order to introduce the data into its memory.

In a particularly advantageous manner, the device according to the invention is also used for programming a pump whose pump unit comprises an electronic memory intended to contain safety data. In this case, the device comprises a second interface which can be connected to the computer in order to receive said safety data and which is designed to be connected to the pump unit in place of the cartridge unit in order to introduce the data into its memory. Preferably, when the energy source is an accumulator, the second interface is also used to recharge this.

In a preferred embodiment, the device according to the invention can be used for programming a pump whose pump unit and cartridge unit are linked by means of a bayonet mount comprising a male part and a female part. In this case, the first interface comprises the same bayonet mount as the pump unit, while the second interface comprises the same bayonet mount as the cartridge unit.

The device according to the invention can be used, especially, for programming a pump in which the memory of the cartridge unit is a SIM (Subscriber Information Memory) card and the pump unit comprises a connector linked to its microprocessor and positioned in such a way that, upon connection of the two units, its contact regions make precise contact with the regions of said SIM card. The first interface of the device thus comprises a connector positioned in such a way that, when the interface and the cartridge unit are joined together, its contact regions make precise contact with the SIM card. In this case, the second interface comprises a connector positioned in such a way that, when the interface and the pump unit are joined together, its contact regions make precise contact with the connector of the pump unit.

The device according to the invention very advantageously comprises means for remote initiation of a two-way transfer of data between the computer and the memory of the cartridge unit.

The invention will be better understood on reading the following description with reference to the attached drawing, in which.

Figure 1:
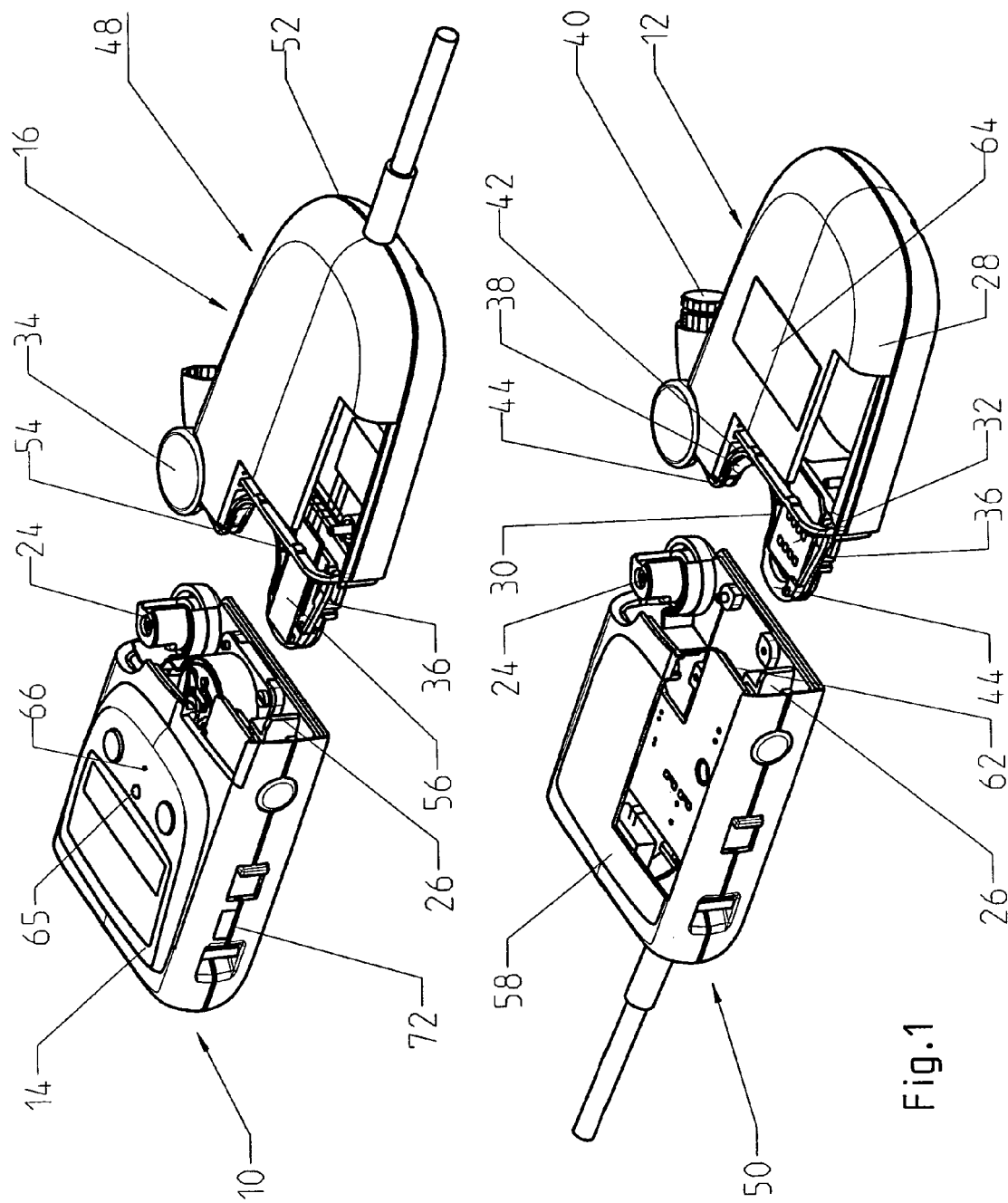
FIG. 1 shows the two interfaces of the programming device and the manner in which they are connected to the two units of the programmable pump.

FIG. 1 shows a pump for administering medicaments, said pump being made up of a pump unit 10 and of a cartridge unit 12 which are connected to one another in a detachable manner via a bayonet mount. As would be familiar to those of ordinary skill in the art, a bayonet mount conventionally comprises a male part and a female part, the male part having one or more prongs or bayonets on a (typically outer) circumference thereof which is/are engaged by rotation into complementary notches in (typically an inner circumference of) the female part. Bayonet mounts are very commonly utilized for secure but releasable attachment of two mechanical components, particularly when, as here, the resulting engagement results in precise alignment of one component with respect to another. In the figure, the two units are shown separately.

The pump is the one forming the subject of the aforementioned European patent application. It will therefore not be described in detail.

It will suffice to indicate that the pump unit 10 reveals, on the open side of its casing 14:
- a metal plate 16 serving as a base for a peristaltic rotary pump head 18 with three press rollers;

the end of a printed circuit 20 equipped with a connector 22 permitting electrical connection of the pump unit to the outside and serving as an interconnection support to a microprocessor and a memory intended to record safety data;

the male part 24 of the bayonet mount; and the first part 26 of a lock securing the two units together.

The pump unit 10 also houses an accumulator (not shown in the figure) intended to power it.

The cartridge unit 12 comprises, inside a casing 28, a matching piece 30 equipped, on the open side of the casing, with:

a smart card 32 of the SIM type (Subscriber Information Memory), intended to record data relating to the prescribed injection program and the history of use of the pump;

the female part 34 of the bayonet mount; and the second part 36 of the lock.

The cartridge unit 12, itself also described in detail in the aforementioned EP document, encloses a pouch acting as a reservoir of medication (not shown in the figure) which a flexible tube 38 links to a connector 40 intended to connect a flexible tubing ending in an injection needle used to administer the medicament contained in the cartridge.

The flexible tube 38 is fitted on the matching piece 30 which takes up the entire width of the casing 28 and is positioned via a groove on its lower shell. The piece 30 comprises, at its center, a rounded concave part 42, of U shape, defining a bearing zone on which, when the two units are joined together and the pump head 18 is rotated, the three press rollers of said pump head alternately squeeze the flexible tube 38 and thus push the liquid contained in the reservoir pouch outward via a peristaltic movement.

The concave part 42 of the matching piece 30 is at the center of two convex parts 44, one of which serves as a support for the SIM card 32 positioned such that, when the two units of the pump are joined together, its contact regions make precise contact with the regions of the connector 22 belonging to the pump unit 10.

The matching piece 30 comprises, beneath the SIM card 32, the second part 36 of the lock and, at its end remote from the one bearing the SIM card, the female part 34 of the bayonet mount.

Figure 2:
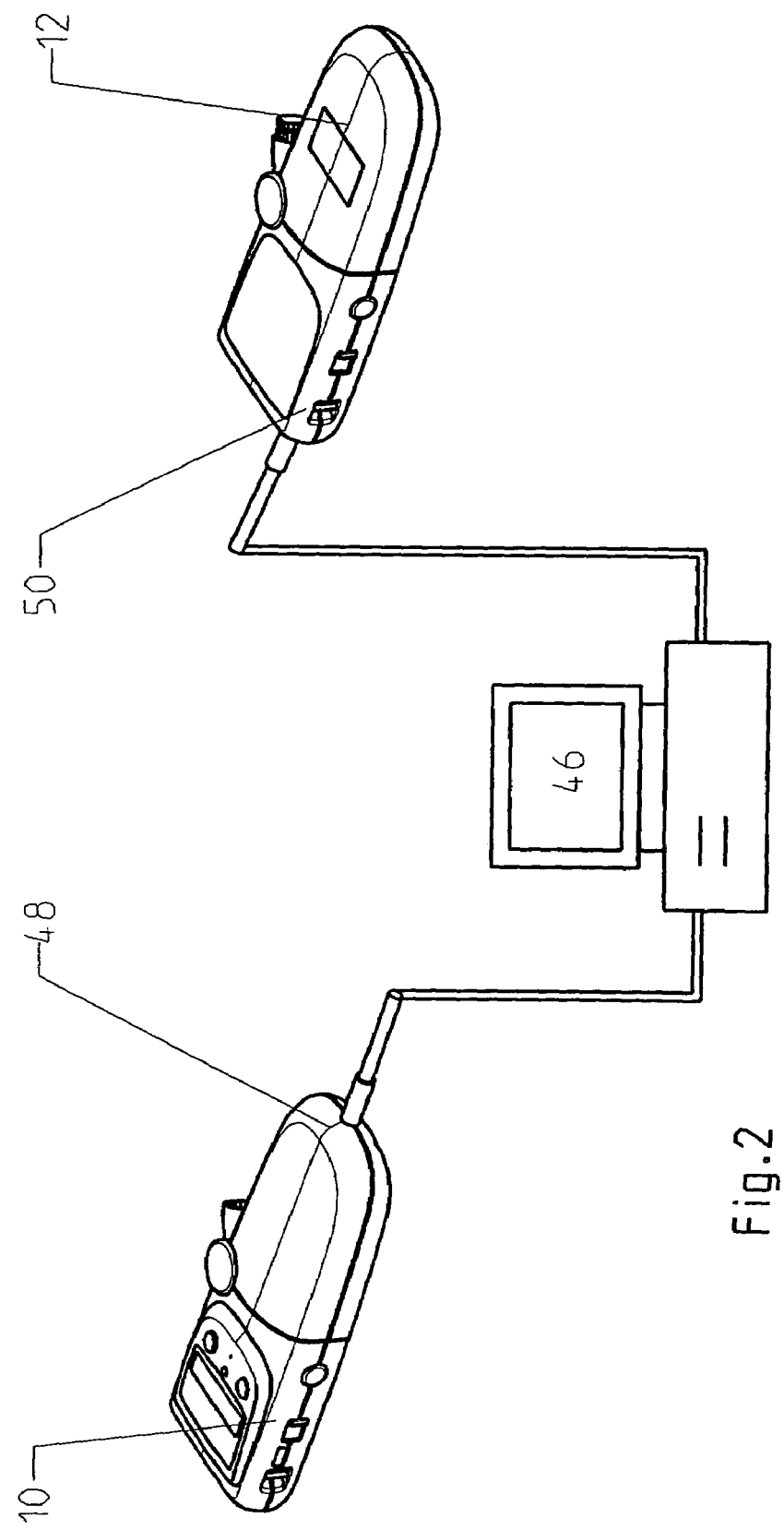
FIG. 2 shows, very schematically, the configuration employed for programming the two units.

According to the invention, as is shown in FIGS. 1 and 2, the programming device comprises:

a computer 46 equipped with software allowing it to communicate with the other elements of the device;

a first interface 48, called the pump interface, intended to connect the computer 46 and the pump unit 10; and a second interface 50, called the cartridge interface, intended to connect the computer 46 and the cartridge unit 12.

The pump interface 48 comprises a casing 52 which, for obvious cost-saving reasons, is the same as the casing 28 of the cartridge unit 12, but without necessarily the 10 connector 40. A joining piece 54, identical to the matching piece 30 and positioned via a groove of the casing 52, thus bears the second part 36 of the lock and the female part 34 of the bayonet mount.

The joining piece 54 serves as a support, in place of the SIM card 32, for a connector 56 whose contact regions are positioned in such a way that, when the interface 48 and the pump unit 10 are connected, they make precise contact with the connector 22 of the pump unit.

The computer 46 is joined to the connector 56, by virtue of which the printed circuit 20 of the pump unit 10 can thus be brought into communication with the computer in order to permit its programming and the recharging of its accumulator.

The cartridge interface 50 comprises a casing 58 identical to the casing 14 of the pump unit 10. It thus bears the first part 26 of the lock and the male part 24 30 of the bayonet mount.

The casing 58 houses a printed circuit 60 whose end, placed at the same site as that of the printed circuit 20 of the pump unit, is equipped with a connector 62 arranged in such a way that, when the interface 50 and the cartridge module 12 are joined together, its contact regions take up a position in which they precisely superpose the SIM card 32 carried by the matching piece 30 of the cartridge unit.

The computer 46 is joined to the connector 62, by virtue of which the SIM card 32 of the cartridge unit 12 can thus be brought into communication with the computer in order to permit its programming.

The computer 46 has been programmed to produce all the safety information which may be required by the medical sector. This typically and chiefly includes the following data:

identification of the patient;

instructions relating to the administration of different medicaments that may possibly be used in the treatment: maximum instantaneous rate of injection, maximum daily injectable quantity, number of boluses authorized per day, maximum volume of each bolus, minimum interval between two boluses, etc.;

possible contraindications or specific intolerance to certain medicaments.

The computer 46 has thus been programmed to produce all the information specific to the treatment that the patient is to receive. This typically and chiefly includes the following data:

identification of the patient;

identification of the medicament to be injected;

instructions relating to the administration of the medicament for the treatment in question: injection program (rates of injection and durations of injection), rates of administration of boluses, their authorized number and interval, etc.

Reference will now be made more particularly to FIG. 2 which illustrates the arrangement of the interfaces 48 and 50, on the one hand, and the units 10 and 12, on the other hand. Thus, when one wishes to program the units with a view to using them, and particularly when the pump unit is being used for the first time, one makes ready:

a pump unit 10, and a cartridge unit 12 taken from the pharmacy stock and identified by a barcode label 64 affixed to the casing 28 and comprising, in coded form and in uncoded form, the type of medicament and its dosage (e.g. morphine 2 g/L) and its volume (e.g. 30 mL).

To program the pump unit 10, it is coupled to the pump interface 48 thus connected to the computer 46, as if coupling the cartridge unit 12 to it. The memory of the pump unit is thus connected to the computer 46, by which means the treatment personnel can simply transfer to it the required safety information, such as the data mentioned above.

Simultaneously, the accumulator of the pump unit 10 is automatically recharged. Advantageously, a monitor 65 can be arranged on the casing 14 in order to supply information on the state of charging of the accumulator.

To program the cartridge unit 12, it is coupled to the cartridge interface 50 thus connected to the computer 46, as if coupling it to the pump unit 10. The SIM card 32 of the cartridge unit is thus connected to the computer 46, by which means the treatment personnel can simply transfer to it the special information relating to the treatment.

The two units 10 and 12 are thus programmed in a very simple manner, the user friendliness of the software avoiding any error to the maximum extent. Advantageously, certain data may be pre-recorded in the software in order to further facilitate the programming.

For a description of the function of the pump when the two units are connected, reference will be made once again to the EP document already cited on several occasions.

According to the invention, it is particularly advantageous for the microprocessor of the pump unit 10 to be programmed to transfer to the SIM card 32 of the cartridge unit 12 the history of use of the pump, that is to say all the changes in state that have been detected: use of the BOLUSES, opening of the pump, stopping of the pump, modification of the flow rate, etc. The SIM card records all this information, often important for the course of treatment, and, at the end of an injection cycle, the physician may gain access thereto. To read the content of the SIM card 32, it suffices for the physician to connect the cartridge unit 12 to the cartridge interface 50 thus connected to the computer 46.

There is another possible way of programming the SIM card 32 of the cartridge unit 12 which can in particular be especially advantageous when the patient is at home and, unable to tolerate the treatment, asks the physician to modify the injection program. In order to avoid a repeat visit which would tire the patient, it is then possible for the treatment personnel to intervene by telephone.

Figure 3:
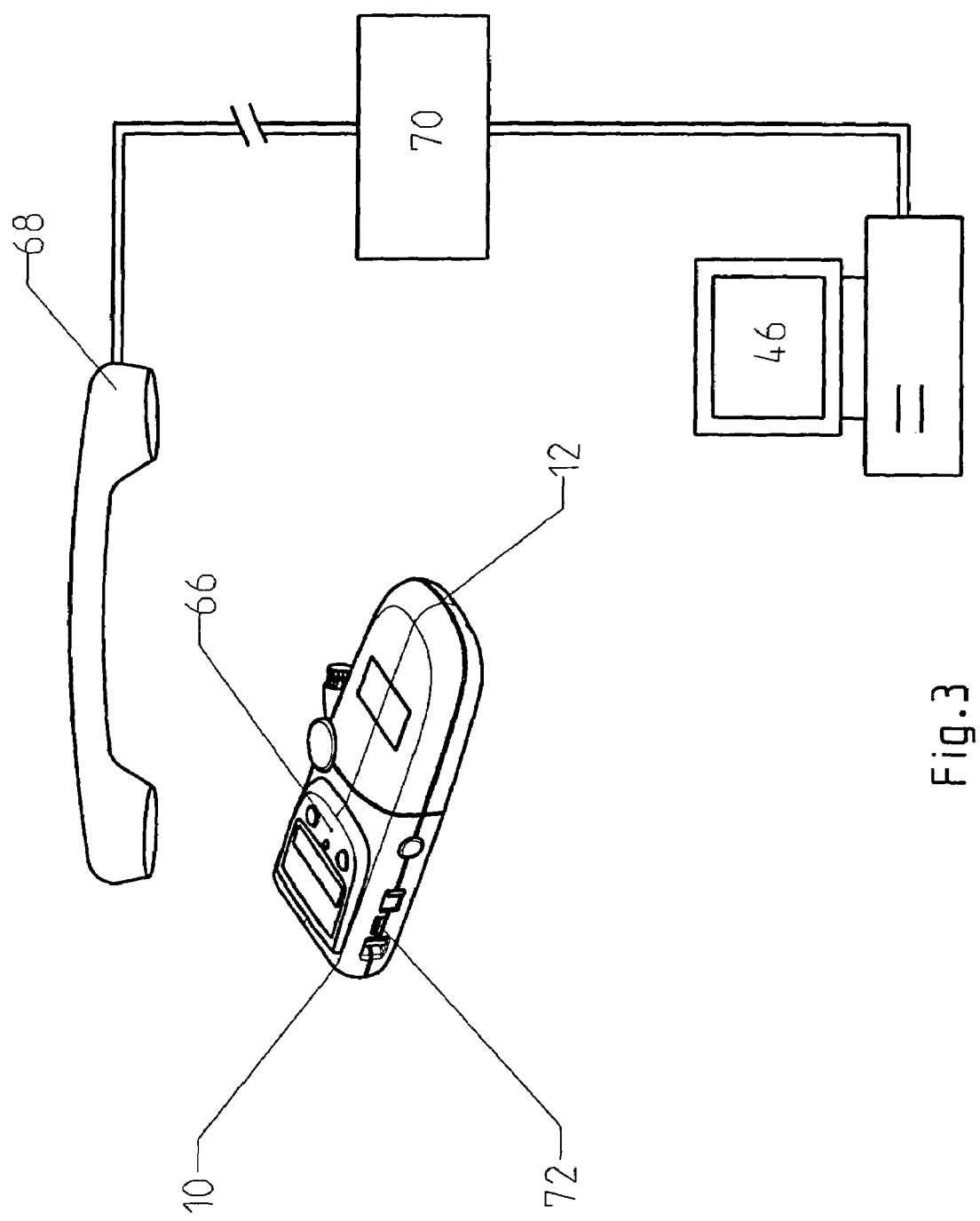
FIG. 3 illustrates the manner of programming the pump by telephone.

To permit such intervention, as is illustrated schematically in FIG. 3, the pump unit 10 is equipped with a microphone 66 connected to its microprocessor and on which the patient can place the speaker of his telephone 68. The personnel providing treatment are for their part equipped with the computer 46 connected to the telephone network by a modem 70.

Using a technique well known to the person skilled in the art of telecommunications, the computer 46 is thus able to transmit, to the microphone 66 of the pump unit 10, coded information corresponding to a modification of the treatment. The signals thus produced by the microphone 66 are received by the microprocessor of the pump unit 10 which transforms them into data significant to the pump. The two units being joined together, said data are transferred by the connector 22 to the SIM card 32 of the cartridge unit 12 in order to replace the initial data relating to the prescribed program. As from that point, the pump unit 10 starts to function according to the new instructions received.

In this method of programming by telephone, it is advantageous, for safety reasons, to equip the pump unit 10 with a speaker 72 and to program its microprocessor to emit, in the direction of the microphone of the patient's telephone, acoustic signals which, after conversion, will allow a confirmation to appear on the screen of the computer 46 that the instructions for modification of the treatment have been correctly received.

Finally, it is possible to integrate in the pump unit 10 a GSM telephone unit (GSM=Global System for Mobile communication) which sends, directly to the microprocessor, the data permitting modification of the content of the SIM memory 32. Compared to the acoustic technique mentioned above, the GSM system makes it possible to exchange information at a much greater rate, while at the same time applying a safety code, thus also authorizing two-way transfer of private data relating to the patient.

The invention claimed is:

1. A device for programming a pump used to inject medicaments into the body of a patient to receive a medical treatment, said pump being made up of two both mechanically and electrically connectable units, namely:
    a cartridge unit (12) which contains a liquid to be injected and which comprises a first electronic memory (36) for storing data relating to said treatment, and
    a pump unit (10) comprising actuation means (18) which act on the cartridge unit (12) in order to convey the liquid outward, a microprocessor which is used to control said means using the data contained in said first memory (36), and a source of electrical energy, characterized in that it comprises:
    a computer (46) which is used to produce said data relating to said treatment, and
    a first interface (50) which can be connected to the computer in order to receive said data relating to said treatment and which is designed to be both mechanically and electrically connected to the cartridge unit (12) in place of the pump unit (10) in order to introduce the data into its memory (36).

2. The device as claimed in claim 1, for programming a pump whose pump unit (10) comprises a second electronic memory for storing safety data, characterized in that it comprises a second interface (48) which can be connected to the computer (46) in order to receive said safety data and which is designed to be both mechanically and electrically connected to the pump unit (10) in place of the cartridge unit (12) in order to introduce the safety data into its memory.

3. The device as claimed in claim 2, for programming a pump in which the energy source is an accumulator, characterized in that the second interface (48) is equipped with means for recharging said accumulator.

4. The device as claimed in claim 1, for programming a pump whose pump unit (10) and cartridge unit (12) are linked by means of a bayonet mount comprising a male part and a female part a first of said male part and said female part belonging to said pump unit (10) and a complementary one of said male part and said female part belonging to said cartridge unit (12), characterized in that
    said first interface (50) is linked to said cartridge unit (12) by means of a bayonet articulation comprising comprising said male and female parts;
    and
    said second interface (48) is linked to said pump unit (48) by means of a bayonet mount comprising a first of a male part and a female part belonging to said pump unit and a complementary one of said male cart and said female part belonging to said interface (48).

5. The device as claimed in claim 1, for programming a pump in which the memory of the cartridge unit (12) is a subscriber information memory (SIM) type card (32) with first contact regions and the pump unit (10) comprises a connector (22) with second contact regions linked to said microprocessor and positioned in such a way that, upon connection of said cartridge unit and said pump unit, said first and second contact regions make precise contact, and further characterized in that said first interface (50) comprises a connector (62) having third contact regions positioned in such a way that, when said interface and said cartridge unit (12) are joined together, said third contact regions make precise contact with said first contact regions on said SIM card (32).

6. The device as claimed in claim 5, characterized in that said second interface (48) comprises a connector (56) with fourth contact regions positioned in such a way that, when the second interface and the pump unit (10) are joined together, said second and fourth contact regions make precise contact.

7. The device as claimed in claim 1, characterized in that it comprises means (68, 70) for remote initiation of a transfer of data between the computer (46) and the memory (36) of the cartridge unit (12).

8. The device as claimed in claim 7, characterized in that said transfer of data is in two directions.

* * * * *